Figure 1A:
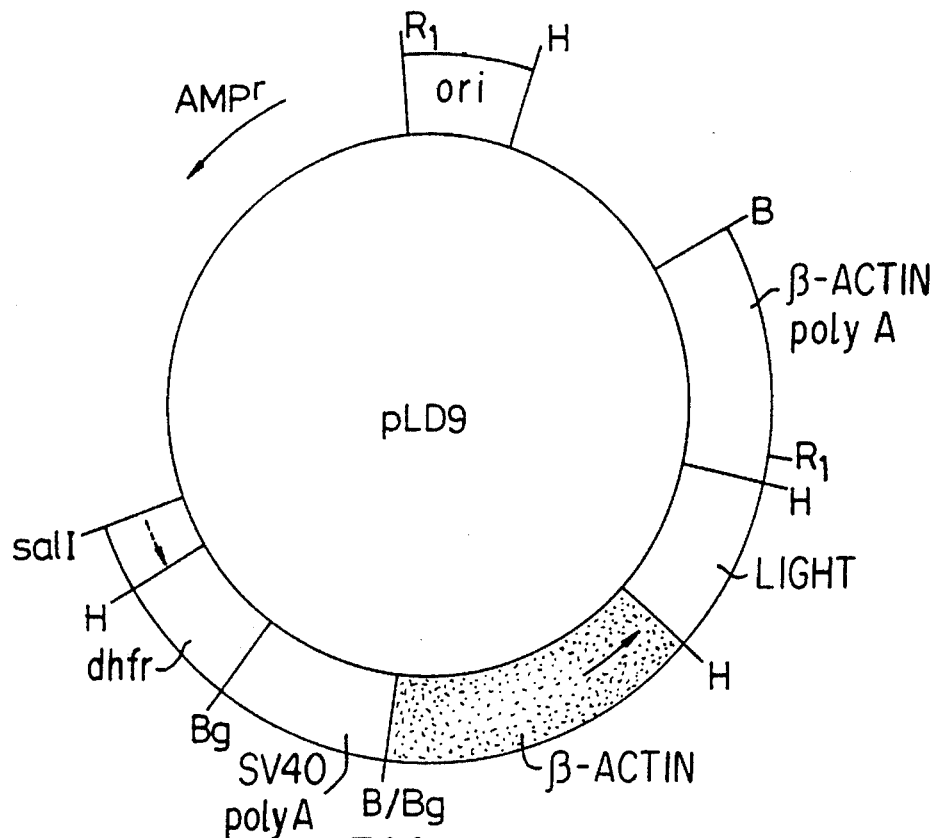

United States Patent [19]
Page

[11] Patent Number: 5,545,405
[45] Date of Patent: *Aug. 13, 1996

[54] METHOD FOR TREATING A MAMMAL SUFFERING FROM CANCER WITH A CHO-GLYCOSYLATED ANTIBODY

[75] Inventor: Martin J. Page, Beckenham, United Kingdom

[73] Assignee: Burroughs Wellcome Co., Research Triangle Park, N.C.

[ * ] Notice: The term of this patent shall not extend beyond the expiration date of Pat. No. 5,545,403.

[21] Appl. No.: 335,401

[22] Filed: Nov. 3, 1994

Related U.S. Application Data

[62] Division of Ser. No. 155,864, Nov. 23, 1993, which is a continuation of Ser. No. 46,893, Apr. 15, 1993, abandoned, which is a continuation of Ser. No. 943,146, Sep. 10, 1992, abandoned, which is a continuation of Ser. No. 777,730, Oct. 16, 1991, abandoned.

[30] Foreign Application Priority Data

Oct. 17, 1990 [GB] United Kingdom ............... 9022543

[51] Int. Cl.⁶ .................. A61K 35/16; A61K 39/00; A61K 39/395; C07K 16/00
[52] U.S. Cl. .................... 424/133.1; 424/130.1; 424/143.1; 424/172.1; 424/174.1; 435/70.3; 435/71.1; 435/240.1; 435/320.1; 530/387.1; 530/388.22; 530/388.73; 530/388.75; 530/388.1; 530/389.1; 530/389.6; 530/389.7
[58] Field of Search .............. 435/240.1, 70.3, 435/71.1, 320.1; 424/130.1, 173.1, 174.1, 143.1, 133.1; 530/387.1, 388.22, 388.73, 388.75, 388.8, 389.1, 389.7, 389.6

[56] References Cited

U.S. PATENT DOCUMENTS

| | | | |
|---|---|---|---|
| 4,816,567 | 3/1989 | Cabilly et al. | 530/387 |
| 5,081,235 | 1/1992 | Shively et al. | 536/27 |
| 5,089,397 | 2/1992 | Kushner et al. | 435/69.1 |
| 5,219,996 | 6/1993 | Bodmer et al. | 530/387.3 |

FOREIGN PATENT DOCUMENTS

| | | | |
|---|---|---|---|
| 0328404 | 2/1989 | European Pat. Off. . | |
| 8901782 | 3/1989 | WIPO . | |
| 89/001783 | 9/1989 | WIPO | A61K 39/395 |
| 9109967 | 7/1991 | WIPO . | |
| 93/07899 | 4/1993 | WIPO | A61k 39/365 |
| 93/10817 | 6/1993 | WIPO | A61K 39/395 |

OTHER PUBLICATIONS

Weidle, U. H., et al., *Gene*, 51: 21–29 (1987).
Feys, V. et al., *Int. J. Cancer*: Supplement 2: 26–27 (1988).
Weidle et al., *Gene*, 60:205–216 (1987).
Nakatani et al., *Bio/Technology*, 7:805–810 (1989).
Gillies et al., *Bio/Technology*, 7:799–804 (1989).
Kaufman et al., *Mol. Cell. Biol.*, 5:1750–1759 (1985).
Zettlmeissl et al., *Bio/Technology*, 9:720–725 (1987).
Page, M. J. et al., *Bio/Technology*, 9 (Jan. 1991).
Goochee and Monica, *Biotechnology* 8 (1990), pp. 421–427.
Leatherbarrow et al., *Molecular Immunology* 22 (1985), pp. 407–415.
Nose and Wigzell, *Proc. Nat. Acad. Sci* 80 (1983), pp. 6632–6636.
Waldmann [Science 252:1657–1662 (1991)].
Harris et al. [TIBTECH 11:42–44 (1993)].
Osband et al. [Immunotherapy 11(6):193–195 (1990)].
Dillman [Ann. Internal Med. 111:592–600 (1989)].
Hird et al. [Genes and Cancer (1990) chapter 17].
Curti [Critical Reviews in Oncology/Hematology 14:29–39 (1993)].
Alessio et al. [Nature 320:449–451 (1986)].
Riechmann et al. [Nature 332:323–327 (1988)].
Borrebaeck et al. Immunology Today 14(19):477–479 (1993).
Galili Immunology Today 14(10):480–482 (1993).
Emmery et al. Exp. Opin. Invest. Drugs 3(3):241–251 (1994).
Rademacher et al. Ann. Rev. Biochem. 57:785–838 (1988).
Hale Progress Report–MRC Wellcome Therapeutic Antibody Centre (1990).
Hale et al. Lancet 394–399 (Dec. 17, 1988).
Lim et al. Lancet 341:432–433 (1993).
Lockwood et al. Lancet 341:1620–1622 (1993).
Poynton et al. Lancet 341:1037 (1993).

*Primary Examiner*—Margaret Parr
*Assistant Examiner*—Donald E. Adams
*Attorney, Agent, or Firm*—Rothwell, Figg, Ernst & Kurz

[57] ABSTRACT

The invention relates to a CHO cell-line capable of producing antibody, the cell-line having been co-transfected with a vector capable of expressing the light chain of the antibody and a vector capable of expressing the heavy chain of the antibody wherein the vectors contain independently selectable markers; also included is a CHO cell-line capable of producing a human antibody or an altered antibody, the cell-line having been transfected with a vector capable of expressing the light chain of the antibody and the heavy chain of the antibody; process for the production of antibody using a CHO cell-line and antibody having CHO glycosylation.

9 Claims, 5 Drawing Sheets

METHOD FOR TREATING A MAMMAL SUFFERING FROM CANCER WITH A CHO-GLYCOSYLATED ANTIBODY

This is a division of application Ser. No. 08/155,864, filed Nov. 23, 1993, which is a continuation of Ser. No. 08/046,893, filed Apr. 15, 1993, now abandoned, which is a continuation of Ser. No. 07/943,146, filed Sep. 10, 1992, now abandoned, which is a continuation of Ser. No. 07/777, 730, filed Oct. 16, 1991, now abandoned.

The present invention relates to Chinese hamster ovary (CHO) cell lines, to the production of proteins, in particular antibodies from such cell lines, also to antibodies having CHO glycosylation.

Antibodies or immunoglobulins are proteinaceous bifunctional molecules. One region which is highly variable between different antibodies is responsible for binding to an antigen (Fab region), for example the many different infectious agents that the body may encounter, whilst the second, constant region (or Fc region) is responsible for binding to the Fc receptors of cells and also activates complement. In this way, antibodies represent a vital component of the immune response of mammals in destroying foreign microorganisms and viruses.

An antibody molecule is composed of two light chains and two heavy chains that are held together by interchain disulphide bonds. Each light chain is linked to a heavy chain by disulphide bonds and the two heavy chains are linked to each other by disulphide bonds. Each heavy chain has at one end a variable domain followed by a number of constant domains, and each light chain has a variable domain at one end and a constant domain at the other end. The light chain variable domain is aligned with the variable domain of the heavy chain. The light chain constant domain is aligned with the first constant domain of the heavy chain. The remaining constant domains of the heavy chains are aligned with each other. The constant domains in the light and heavy chains are not involved directly in binding the antibody to the antigen.

The variable domains of each pair of light and heavy chains form the antigen binding site. They have the same general structure with each domain comprising a framework of four regions, whose sequences are relatively conserved, connected by three complementarity determining regions (CDRs). The four framework regions largely adopt a beta-sheet conformation and the CDRs form loops connecting, and in some cases comprising part of, the beta-sheet structure. The CDRs are held in close proximity by the framework regions and, with the CDRs from the other domain, contribute to the formation of the antigan binding site.

The immunisation of an animal with an antigen results in the production of different antibodies with different specificities and affinities. An antiserum obtained from the immunised animal will, therefore, be heterogeneous and contain a pool of antibodies produced by many different lymphocyte clones. Antibodies thus obtained are referred to as polyclonal antibodies and this polyclonal nature has been a major drawback in the use of antibodies in diagnostic assays and in therapeutic applications.

A major step forward occurred in 1975 when Kohler and Milstein (*Nature,* 1975, 256, 495–497) reported the successful fusion of spleen cells from mice immunized with an antigen with cells of a murine myeloma line. The resulting hybrid cells, termed hybridomas, have the properties of antibody production derived from spleen cells and of continous growth derived from the myeloma cells. Each hybridoma synthesizes and secretes a single antibody to a particular determinant of the original antigen. To ensure that all cells in a culture are identical, i.e. that they contain the genetic information required for the synthesis of a unique antibody species, the hybridomas resulting from cell fusion are cloned and subcloned. In this way, the cloned hybridomas produce homogeneous or monoclonal antibodies.

The advantages of hybridoma technology are profound. Because many hybrids arising from each spleen are screened for their potential to produce antibodies to the antigan of interest and only a few are selected, it is possible to immunize with impure antigens and yet obtain specific antibodies. The immortality of the cell line assures that an unlimited supply of a homogeneous, well-characterised antibody is available for use in a variety of applications including in particular diagnosis and immunotherapy of pathological disorders.

Unfortunately, the usefulness of such monoclonal antibodies in a clinical setting can be severely hampered by the development of human anti-mouse antibodies—an antiglobulin response—which may interfere with therapy or cause allergic or immune complex hypersensitivity.

When, for example, murine (or ratine) monoclonal antibodies are used in human therapy, the induction of an human anti-mouse antibody response is due to the murine origin of the constant domains and four framework regions. This problem has therefore been addressed by the development of antibodies of two basic types. The first type, referred to as chimeric antibodies, is where the murine constant domains only are replaced by equivalent domains of human origin (Morrison et al, P.N.A.S., 1984, 81, 6851–6855; Boulianne et al, *Nature,* 1985, 314, 268–270; and Neuberger et al, *Nature,* 1985, 314, 268–270). The second type is where the murine constant domains and the murine framework regions are all replaced by equivalent domains and regions of human origin. This second type of antibody is referred to as a humanised or CDR-grafted antibody (Jones et al, *Nature,* 1986, 321, 522–525; and Riechmann et al, *Nature,* 1988, 332, 323–327). A human antibody would of course avoid the need for "humanisation", however cell lines which secrete human antibodies are very unstable and have generally proven unsuitable for commercial scale production.

To generate sufficient quantities of antibody for full clinical use it is desirable to employ an efficient recombinant expression system. Since myeloma cells represent a natural host specialized for antibody production and secretion, cell lines derived from these have been used for the expression of recombinant antibodies. Often, complex vector design, based around immunoglobulin gene regulatory elements, is required, and final expression levels have been reported which are highly variable (Winter et al, *Nature,* 1988, 332, 323–327; Weidle et al, *Gene,* 1987, 60, 205–216; Nakatani et al, *Bio/Technology,* 1989, 7, 805–810; and Gillies et al, *Bio/Technology,* 1989, 7, 799–804).

An alternative mammalian expression system is that offered by the use of dihydrofolate reductase (dhfr) deficient Chinese hamster ovary (CHO) cells. The use of these cells has enabled the production of large quantities of several therapeutic proteins for research and clinical use (Kaufman et al, *Mol. Cell. Biol.,* 1985, 5, 1750–1759; and Zettlmeissl et al, *Bio/Technology,* 1987, 5, 720–725). There are, however, very few instances of the use of these cells for the expression of antibodies and the levels of expression of murine antibodies reported to date are low—of the order of 0.01–0.1 µg/ml (Weidle et al, *Gene,* 1987, 51, 21–29; and Feys et al, *Int. J. Cancer,* 1988, 2, 26–27).

A process has now been developed that enables the balanced expression of the light and heavy chains of an antibody from CHO cells. Balanced expression is desirable given that the light and heavy chains are linked together in the antibody molecule in equimolar proportions. This process allows the antibody to be obtained in functional form and to be secreted in good yields. Thus the process enables sufficient quantities of functional antibody to be obtained for use in the immunotherapy of pathological disorders.

The invention therefore provides a CHO cell line capable of producing antibody, the cell line having been co-transfected with a vector capable of expressing the light chain of the antibody and a vector capable of expressing the heavy chain of the antibody wherein the vectors contain independently selectable markers.

The present invention further provides a CHO cell line capable of producing a human antibody or an altered antibody, the cell line having been co-transfected with a vector containing cDNA encoding the light chain of the antibody and a vector containing cDNA encoding the heavy chain of the antibody said vectors capable of expressing the light and heavy chains of the antibody. The vectors may advantageously contain independently selectable markers. Hereafter, reference to the markers includes the singular and vice versa.

The cell line of the present invention is capable of producing all kinds of antibodies that generally comprise equimolar proportions of light and heavy chains. The invention therefore includes human antibodies wherein the amino acid sequences of the heavy and light chains are homologous with those sequences of antibodies produced by human lymphocytes in vivo or in vitro by hybridomas. Also included in the invention are altered antibodies such as hybrid antibodies in which the heavy and light chains are homologous to a natural antibody but are combined in a way that would not occur naturally. For example, a bispecific antibody has antigen binding sites specific to more than one antigen. The constant region of the antibody may relate to one or other of the antigen binding regions or may be from a further antibody. Altered antibodies, such as chimaeric antibodies have variable regions from one antibody and constant regions from another. Thus, chimaeric antibodies may be species/species chimaeras or class/class chimaeras. Such chimaeric antibodies may have one or more further modifications to improve antigen binding ability or to alter effector functioning. Another form of altered antibody is a humanised or CDR-grafted antibody including a composite antibody, wherein parts of the hypervariable regions in addiron to the CDRs are transferred to the human framework. Additional amino acids in the framework or constant regions of such antibodies may be altered. Included in the definition of altered antibody are Fab fragments which are roughly equivalent to the Y branch portions of the heavy and light chains; these may be included incomplete fragments or fragments including part of the Fc region. Thus, within the scope of the invention is included, any altered antibody in which the amino acid sequence is not one which exists in nature.

The cell line of the invention is preferentially employed for the production of altered antibodies most preferably chimaeric antibodies or CDR-grafted antibodies. Particular examples of these include antibodies against T cell markers such as CD2, CD3, CD4, CD5, CD7, CD8, CD11a, CD11b, CD18, CD19, CD25, CD45 and CDw52 and especially CDR grafted antibodies against the CDw52 antigen, such as Campath-1H (Campath is a Trademark of the Wellcome Foundation Ltd) described in EP 328404 Further examples include CDR-grafted antibodies against various cancer cell marker antigens such as CD33 and CD38.

After co-transfection into recipient CHO cells, the resulting colonies may be selected using both markers. Colonies exhibiting the dual phenotype are generally capable of co-expressing both the light and heavy chains. The selectable markers may or may not be of a dominant nature. Examples of selectable markers for use in co-transfection include adenosine deaminase (Kaufman et al, *P.N.A.S.*, 1989, 83, 3136–40) asparagine synthetase (Cartier et al, *Mol. Cell Biol.*, 1987, 7, 1623–28), *E.coli* trpB gene and Salmonella hisD gene (Hartman et al, *P.N.A.S.*, 1988, 85, 8407–51), M2 mouse ribonucleotide reductase (Thelander et al, *EMBO J*, 1989, 8, 2475–79), human multidrug resistance gene (Kane et al, *Gene,* 1989, 84, 439–446), glutamine synthetase (Bebbington et al, *DNA Cloning*, Vol III, 1987, Ed. D. M. Glover, 163–188, IRL Press), xanthine guanine phosphoribosyl transferase (gpt) (Mulligan et al, *Science*, 1980, 209, 1422–27), hygromycin B (Santerre et al, *Gene*, 1984, 30, 147–156), neomycin gene (Southern et al, *J. Mol. Appl. Genet.*, 1982, 1, 327–341), and dihydrofolate reductase (Subramani et al, *Mol. Cell Biol.*, 1981, 1, 854–864). One particularly preferred selectable marker is dhfr which is usually employed with a parental CHO cell line of the dhfr⁻ phenotype (Urlaub et al, *P.N.A.S.*, 1980, 77, 4216–4220). Successfully co-transfected CHO cells will possess the dhfr⁺ phenotype and can readily be selected by culturing the colonies on media devoid of thymidine and hypoxanthine and optionally containing methotrexate (MTX). A preferred selectable marker for use with the other of the vectors is a dominant resistance marker, such as neomycin (neo). CHO cells successfully transfected with this marker can readily be selected by culturing the colonies on media containing the antibiotic, G418, otherwise known as Geneticin.

A second preferred system of selection and amplification is provided by the glutamine synthetase selectable marker or (GS system) which is described in WO87/04462. CHO cells which have been successfully transfected with the gone encoding the GS enzyme and the desired antibody gene can be selected by culturing colonies in media devoid of glutamine as described in PCT published application number WO87/04462.

At least one of the selectable markers preferably also provides the basis upon which the genes encoding the light and heavy chains may be amplified. In co-transfection of a CHO cell line, the vector DNAs are often integrated into the chromosome of the cell at the same locus. Thus, the use of only one of the selectable markers as the basis for amplification normally results in a parallel increase in the copy number of both genes. One particularly preferred selectable marker for use in this way is dhfr which enables the desired amplification to be obtained through the use of increasing concentrations of MTX. A second preferred selectable marker is GS which allows amplification by the addition of methionine sulphoximine (MSX).

The selectable markers are of course under the control of regulatory elements of DNA so as to provide for their expression. In the case of the use of dhfr as a selectable marker, the regulatory elements are preferably of a viral source, such as from DNA tumour viruses. Particularly preferred are the use of an SV40 or adenovirus major late promoter. It is particularly advantageous in this regard to remove the enhancer element from the promoter thus effectively "crippling" it. This modification allows for increased levels of gene amplification at each concentration of methotrexate selection than would otherwise occur if a strong promoter was used. In the case of the use of neo as a selectable marker, an example of a suitable promoter is the mouse metallothionein promoter.

The light and heavy chain genes may constitute genomic DNA or, preferably, cDNA, and are cloned using procedures known in the art (Molecular Cloning: A Laboratory Manual, Second Edition, Maniatis et al, Cold Spring Harbor). The genes are also under the control of regulatory elements of DNA so as to provide for their expression. The use of the same regulatory elements for both chains is preferred so that their expression is substantially balanced. The regulatory elements may be of viral origin and examples include those mentioned above in conjunction with the expression of dhfr as a selectable marker. Another example is the use of the β-actin promoter and cognate β-actin polyadenylation signal.

One or both of the vectors may also contain an SV40 origin of replication to allow for the vector constructs to be checked by rapid transient assay.

Construction of the expression vectors may be carried out in accordance with procedures known in the art (Molecular Cloning: A Laboratory Manual, Second Edition, Maniatis et el, Cold Spring Harbor).

Co-transfection of the CHO cell line with the expression vectors may be carried out simply by using equimolar quantities of both vectors and standard transfection procedures, such as calcium phosphate precipitation or lipofectin. Selection of the desired co-transfected cell line may be carried out in accordance with standard procedures known for the particular selectable markers.

The present invention also provides a process for the production of an antibody which comprises culturing a CHO cell line of the present invention. Culture of the CHO cell line may be carried out in serum-containing or preferably serum and protein free media. In one preferred instance where the CHO cell line is a dhfr$^+$ transformant, the medium preferably lacks hypoxanthine and/or thymidine and optionally contains MTX. Where a selectable marker is glutamine synthetase the medium preferably lacks glutamine and optionally contains MSX. Expression of both chains in substantially equimolar proportions enables optimum yields of functional antibody to be obtained. The two chains assemble within the cell and are then secreted into the culture medium as functional antibody. The resulting antibody may be purified and formulated in accordance with standard procedures.

Antibodies are glycoproteins containing between 3 and 12% carbohydrate. The carbohydrate units are transferred to acceptor sites on the antibody chains after the heavy and light chains have combined. The major carbohydrate units are attached to amino acid residues of the constant region of the antibody. Carbohydrate is also known to attach to the antigen binding sites of some antibodies and may affect the antibody-binding characteristics by limiting access of the antigen to the antibody binding site. There are a number of roles associated with the carbohydrate units. They may affect overall solubility and the rate of catabolism of the antibody. It is also known that carbohydrate is necessary for cellular secretion of some antibody chains. It has been demonstrated that glycosylation of the constant region plays a vital role in the effector functioning of an antibody; without this glycosylation in its correct configuration, the antibody may be able to bind to the antigen but may not be able to bind for example to macrophages, helper and suppressor cells or complement, to carry out its role of blocking or lysing the cell to which it is bound.

It has now been found that antibody glycosylated by CHO cells maintains antigen binding capability and effector functionality. This has been demonstrated in in vitro complement lysis assays and in vivo in a human patient.

The invention therefore provides an antibody having CHO glycosylation. Such antibodies may be natural, such as human antibodies, altered antibodies for example hybrid antibodies or bispecific antibodies, chimaeric or CDR-grafted antibodies, including Fab fragments.

The CHO glycosylation may be associated with the antigen binding site or other parts of the variable domain. It may alternatively or additionally be associated with the constant region. The glycosylated antibody is prepared by expression of the antibody genes in a suitably engineered CHO cell followed by recovery and if necessary, purification of the antibody from the cell culture medium.

CHO glycosylated antibodies are useful in medical therapy for treating numerous human disorders, generally as immunosuppressives more particularly for example T-cell mediated disorders including severe vasculitis, rheumatoid arthritis, systemic lupus, also autoimmune disorders such as multiple sclerosis, graft vs host disease, psoriarsis, juvenile onset diabetes, Sjogrens' disease, thyroid disease, myasthenia gravis, transplant rejection and asthma. These antibodies are also useful in treating cancer such as Non-Hodgkins lymphoma, multiple myeloma, and infectious diseases such as HIV and herpes.

The invention therefore provides the use of CHO glycosylated antibodies in the manufacture of a medicament for the treatment of any of the aforementioned disorders. Also provided is a method of treating a human being having any such a disorder comprising administering to said individual a therapeutically effective amount of a CHO glycosylated antibody.

The dosages of such antibodies will vary with the condition being treated and the recipient of the treatment, but will be in the range 1 to about 100 mg for an adult patient preferably 1–10 mg usually administered daily for a period between 1 and 30 days. A two part dosing regime may be preferable wherein 1–5 mg are administered for 5–10 days followed by 6–15 mg for a further 5–10 days.

Also included within the invention are formulations containing CHO glycosylated antibody. Such formulations preferably include, in addition to antibody, a physiologically acceptable diluent or carrier possibly in admixture with other agents such as other antibodies or an antibiotic. Suitable carriers include but are not limited to physiological saline, phosphate buffered saline, phosphate buffered saline glucose and buffered saline. Alternatively, the antibody may be lyophilised (freeze dried) and reconstituted for use when needed by the addition of an aqueous buffered solution as described above. Routes of administration are routinely parenteral including intravenous, intramuscular, subcutaneous and intraperitoneal injection or delivery.

Figure 1B:
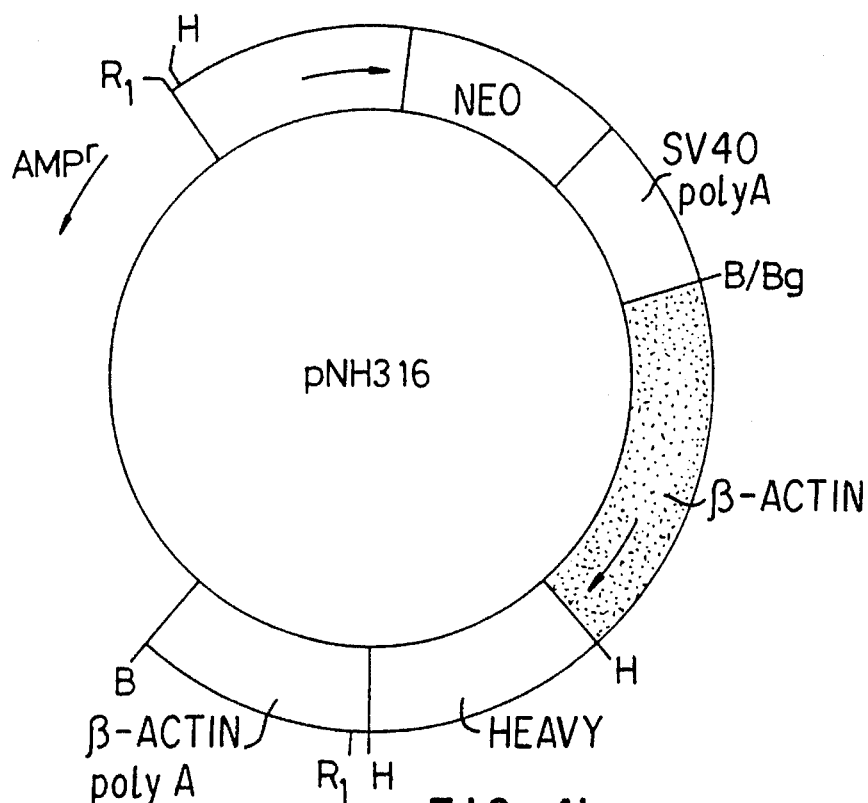

The accompanying drawings show:

FIGS. 1(a) and 1(b)

(a) the pLD9 construct containing expression cassettes for the 'crippled' dhfr selection/amplification marker and the Campath-1H light chain cDNA. The small box with the dashed arrow is the weakened SV40 promoter; the larger dotted box with an arrow is the β-actin promoter; polyA refers to respectively sourced polyadenylation and termination signals; the small box with ori contains the SV40 origin of replication; (b) the pNH316 construct containing expression cassettes for the neomycin selection marker and the Campath-1H heavy chain cDNA. The box with an arrow and MT refers to the mouse metallothionein promoter. Restriction sites indicated are:- H, HindIII; Bg, BglII; B, BamHI; R1, EcoR1.

FIG. 2

Comparative determinations of the rate of Campath-1H synthesis in confluent A39 cells over 4 consecutive days. Following the [$^{35}$S] methionine pulse period, equal aliquots of cells (C) and culture medium (M) were immuno-precipitated and separated by SDS-PAGE. The position of the Campath-1H heavy and light chains are indicated (H and L arrows). There was some loss of material for the day 3 cell sample.

FIG. 3

A pulse-chase experiment to determine the rate of secretion and distribution of radiolabelled Campath-1H in A39 cells. Confluent cells were pulsed with [$^{35}$S] methionine for 6 hours, then fresh medium containing an excess of unlabelled methionine was added. Equal aliquots of cells and culture medium were taken at the indicated time points (in hours following the end of the pulse period) and treated as described in the legend of FIG. 2. The samples for the 48 and 72 hour medium time points were run on a different gel to the 6 and 24 hour points, and the tracks are only lined up relative to the position of the heavy (H) chain.

FIG. 4

Shows growth of C1H 3D11* 44 in WCM5 (protein-free medium) in a 1 liter farmenter measured as cell count/ml over 90 days.

FIG. 5

Shows antibody production from C1H 3D* 44 cells in WCM5 in a 1 liter fermenter measured as micrograms of antibody/ml over 80 days.

The following Examples are provided purely for illustration of the present invention.

EXAMPLE 1

Cloning of the Heavy and Light Chain cDNAs for Campath-1H

The complementarity determining regions from the rat Campath-1G monoclonal were originally grafted directly into genomic human heavy and light chain frameworks (Winter et al, *Nature*, 1988, 322, 323–327). These constructs were engineered for expression in the myeloma cell line Y0 and resulted in yields of Campath-1H of up to 5 μg/ml following 10–14 days in culture (Hale et al, *Tissue Antigens*, 1990, 35, 118–127 and Winter et al, *Nature*, 1988, 322, 323–327). The myeloma cell line TF57 (Hale et al, ibid,) was used to generate size selected cDNA fractions of 0.9–1.2 kb and 1.4–1.7 kb for the light and heavy chain cDNAs respectively. These were used to make EcoR1 linkered cDNA libraries in λgt10. All procedures were as described by Huynh et al (*DNA Cloning*, Vol I: A Practical Approach, 1984, Glover, D(Editor), IRL Press,Oxford). The libraries were screened using [$^{32}$P] nick translated probes specific for the variable regions to isolate full length cDNA clones. For the light chain cDNA, the 5' untranslated leader was removed up to position −32 using Bal-31 exonuclease and a HindIII linker added. For the 3' end, use was made of a unique SacI site 47 bp upstream of the stop codon. A SacI-HindIII oligonucleotide pair was used to regenerate this sequence and position the HindIII site immediately after the stop codon. For the 5' end of the heavy chain cDNA, the unique NcoI site overlapping the ATG start codon was used to re-build a 29 bp unrrahoisted leader, identical to that of the light chain, using a HindIII-NcoI oligonucleotide pair. At the 3' end, the unique NaeI site 12 bp downstream of the stop codon was converted into a HindIII site using linkers.

EXAMPLE 2

Construction of Vectors:

The human β-actin promoter was excised from pHβAPr-3-neo (which corresponds to pHβAPr-1-neo (Gunning et al, *P.N.A.S.*, 1987, 84, 483–35) except that the SV40 polyadenylation/termination signal has been replaced with the respective human β-actin signals) as a 2860 bp PvuII-HindIII fragment, in which the PvuII site was subsequently converted to a BglII site using linkers. To isolate the human β-actin polyadenylation and termination signals from pHβAPr-3-neo, an SphI site 1.4 kb downstream of the unique HindIII site was converted to a BamHI site using linkers. The basal dhfr vector called p104, was constructed as follows. The SphI site at position −128 in the SV40 promoter in pSV2dhfr (Subramani et al, *Mol. Cell. Biol.*, 1981, 1, 854–864) was converted into a SalI site to remove all enhancer elements from the promoter. The weakened dhfr expression unit was then subcloned as a SalI-BamHI fragment into the homologous sites in pSVOd (Mellon et al, *Cell*, 1981, 27, 279–288).

To construct pLD9, the p104 vector was digested with BamHI, phosphatased, and ligated with three other fragments consisting of the BglII-HindIII β-actin promoter, the HindIII Campath-1H light chain cDNA and the HindIII-BamHI β-actin polyA/termination signals. To construct pNH316, the construct pdBPV-MMTneo (Law et al, *Mol.Cell.Biol.*, 1983, 3, 2110–2115) was digested with BamHI, phosphatased, and the fragment containing the neomycin gene isolated following separation on an agarose gel. This was ligated to the two β-actin fragments and the Campath-1H heavy chain cDNA. The constructs, pLD9 and pNH316 are depicted in FIGS. 1(a) and (b), respectively.

EXAMPLE 3

Expression of Campath-1H in CHO Cells:

The dhfr$^-$ CHO cell line DUK-B11 (Urlaub et al, *P.N.A.S.*, 1980, 77, 4216–4220) was grown in Iscove's MEM supplemented with 10% fetal bovine serum, and 4 μg/ml each of hypoxanthine and thymidine. 10 μg of pLD9 and pNH316 was co-precipitated onto cells using the calcium phosphate method, (Gorman et al, *DNA Cloning*, 1985, Vol II, 143–190, Academic Press, N.Y.) and selected for the double phenotype of dhfr$^+$/neo resistance by using the medium above except that 10% dialysed serum was used, the hypoxanthine/thymidine were omitted, and G418 (Gibco) was included at 500 μg/ml. In some experiments MTX was included directly in the first round selection for dhfr$^+$ trans formants. Several hundred resistant colonies were pooled and assayed for the production of Campath-1H antibody in the culture medium. The average yield was 0.5 μg/ml for non-amplified first round trans formants.

Each pooled cell population was then cultured in the presence of $10^{-7}$M MTX, and after two weeks, resistant colonies were again pooled and titred for Campath-1H production. There was a considerable increase in yield of up to 80-fold (Table 1). These cells were dilution cloned, screened for Campath-1H yield, and two high producer lines isolated, called A37 and 3D9 (Table 1). These were both amplified further in the presence of $10^{-6}$M MTX, then dilution cloned and screened as above. The increase in expression at this second, and final, amplification stage was not so dramatic as seen previously; nevertheless, when re-fed at confluence and left for a further 4 days, the cell lines A39 and 3D11 were capable of producing up to 200 μg/ml of Campath-1H.

TABLE 1

| Expression Levels of Campath-1H using Stepwise Amplification | | |
|---|---|---|
| Construct | Selection stage | Accumulated Campath-1H (μg/ml) |
| pLD9 + | dhfr$^+$/neo basal pool | 0.5 |

TABLE 1-continued

Expression Levels of Campath-1H using Stepwise Amplification

| Construct | Selection stage | Accumulated Campath-1H (μg/ml) |
|---|---|---|
| pNH316 | $10^{-7}$M MTX amplified pool | 18–40 |
|  | Cell lines A37 and 3D9 | 40 |
|  | $10^{-6}$M MTX amplified pool | 60–90 |
|  | Cell line A39 | 100 |
|  | Cell line 3D11 | 150–200 |

Legend to Table
Cells were allowed to reach confluence in a T-175 tissue culture flask, then re-fed with fresh 50ml of tissue culture medium and left for a further 4 days. The Campath-1H antibody that had accumulated in the medium during this period was measured by ELISA. Total cell counts on the day of assay were usually $2.5 \times 10^7$. The yield from the 3D11 cell line reflects a productivity of 100 μg/$10^6$ cells/day.

The co-transfection vectors pLD9 and pNH316 were further employed to evaluate an alternative amplification strategy to the one described above. The dhfr⁻ CHO cells were co-transfected as usual, and two days later split directly into a series of flasks containing G418 (for neomycin selection) and increasing concentrations of MTX ranging from $3\times10^{-9}$M to $10^{-7}$M. Following two weeks of this selection, the number of resistant colonies were counted and pooled for each flask. When the cell populations had stabilized, they were assayed for Campath-1H antibody titres and the results are shown in Table 2. As the MTX level was increased, there was a marked decrease in the number of surviving dhfr⁺ colonies, but they expressed proportionately more Campath-1H. Thus, in a one step direct selection at high concentrations of MTX, it is possible to isolate cell populations which produce up to 60-fold increase in antibody yield compared to cell populations selected for basal dhfr levels.

TABLE 2

Expression Levels of Campath-1H using Direct Selection

| Selection (M MTX) | dhfr⁺ colonies | Accumulated Campath-1H (μg/ml) |
|---|---|---|
| No MTX | 500 | 0.5 |
| $3 \times 10^{-9}$ | 40 | 2 |
| $10^{-8}$ | 5 | 7 |
| $3 \times 10^{-8}$ | 5 | 30 |
| $10^{-7}$ | — | — |

Legend to Table
colonies at each MTX selection stage were pooled and assayed as described in the legend of Table 1.

This selection procedure was repeated following another co-transfection of cells, and in this instance, the entire population was selected in medium containing G418 and $3\times10^{-8}$M MTX. This generated a larger pool of resistant colonies which were subsequently pooled and re-amplified twice more using MTX concentrations of $6\times10^{-7}$M, then $3\times10^{-6}$M. At this stage, the cells were dilution cloned and screened for Campath-1H levels. The two highest producer cell lines isolated were capable of producing antibody levels up to 100–150 μg/ml and were designated as lines 4F11 and 5E10.

The growth rates of these cell lines, and the A39/3D11 lines described above, were considerably slower than the parental non-transformed dhfr⁻ CHO cells. This is usually a common feature of these cells once they have been engineered to express high quantities of a product gene. The yields from the 5E10 and 4F11 cell lines proved to be quite variable over time, and the latter appeared to have only a limited passage life lasting about 3 weeks before entering crisis and death. This instability was not evident at all in the other cell lines, although in general, the lines isolated from the second amplification procedure, including 5E10, were usually more fickle co culture. Of all the lines, the 3D11 coupled good growth and stability with high Campath-1H yields. To ensure the propagation of these features, the 3D11 cell line was dilution cloned once more to generate the 3D11* line and this similarly produced Campath-1H yields up to 200 μg/ml.

EXAMPLE 4

Growth of and Production from C1H 3D11* 44 in WGM4 a) C1H 3D11* cells growing as a monolayer in Iscoves+ 10% FBS Flow, non-essential amino acids, $10^{-6}$M Methotrexate and antibiotics were approximately 90% confluent. These cells were removed from the plastic with trypsin/versene, washed in Iscoves medium without supplements, centrifuged and resuspended at $5\times10^4$/ml in WCM4 medium Table 3+0.25% peptone+0.1% polyethylene glycol (PEG) 10,000+0.5% fetal boine serum (FBS) without methotrexate (MTX).

TABLE 3

Formulation for medium WCM4
Iscoves modification of DMEM without BSA, transferrin and lecithin. Available from GIBCO Ltd., Unit 4, Cowley Mill Td. Est., Uxbridge UB8 27G. Similar to published medium (Iscoves and Melcher (1978) J. Exp. Med. 1. 47, 923) without the bovine serum albumin, pure human tranferrin, or soyabean lecithin.

| | | |
|---|---|---|
| + | 5 ml/liter | 200mM L glutamine |
| + | 50 mg/liter | L proline |
| + | 50 mg/liter | L threonine |
| + | 50 mg/liter | L methionine |
| + | 50 mg/liter | L cysteine |
| + | 50 mg/liter | L tyrosine |
| + | 25 mg.liter | ascorbic acid |
| + | 0.062 mg.liter | vitamin B6 |
| + | 1.36 mg.liter | vitamin B12 |
| + | 0.2 mg/liter | lipoic acid |
| + | 0.088 mg/liter | methyl linoleate |
| + | 1 μM | methotrexate |
| + | 1 mg/liter | FeSO₄ |
| + | 1 mg/liter | ZnSO₄ |
| + | 0.0025 mg/liter | CuSO₄ |
| + | 5 mg/liter | recombinant insulin (Nucellin) |
| + | 50,000 Iu/liter | polymyxin |
| + | 20,000 Iu/liter | neomycin |
| + | 0.16 mg/liter | putrescine-2 HCL. |

Three 25 cm² flasks were set up with 10 ml of cell suspension+hypoxanthine (H), thymidine (T) or HT. These flasks were incubated at 36.5° C. in 5% $CO_2$ incubator.

After six days, the flasks were pooled and added to an equal volume of WCM4+MTX without peptone or PEG, and were transferred to a 75 cm² flask.

These cells ware used to seed a 500 ml Techner spinner, incubated at 36.5° C. spinning at 40 rpm. Cells continued growing serum free for a period of over five months and although it was found that the cells needed a period of adaptation, the growth rate and viability steadily improved. The population doubling time was calculated to be 73.1 hours over approximately 7 weeks; this decreased to 47.4 hours over the subsequent 20 days then stabilised. Antibody secretion remained high at levels in excess of 60 μg/ml. It was determined that the gene copy number in these cells did not decrease according to band intensity using Northern blot analysis.

In fermentars, these cells produced antibody in excess of 70 μg/ml and regularly achieve levels of 100 μg/ml or more. These cells are denoted C1H 3D11 44.

b) Cells from a) above which had been growing serum-free for over 2 months ware transferred to a SGi 1 liter fermenter with a stainless steel angled paddle turning at 70 rpm. The temperature was set at 37° C., dO$_2$ at 10% and pH control to 7–7.2. The fermenter was seeded on day 0 with 0.22×10$^6$ cells/ml in WCM4 (Table 3) with 0.1% polyethylene glycol (PEG) 10,000 and 0.25% soy peptone, and was top gassed with O$_2$. The cells were routinely passaged using fresh medium and a split rate typically between 1 to 2 and 1 to 4.

On day 33 the top gassing was replaced with deep sparging which is can be expected to cause more physical damage to the cells.

On day 50 onwards WCM5 (Table4) was used together with peptone and PEG instead of WCM4.

TABLE 4

Formulation for Medium WCM5
Iscoves modification of DMEM without BSA, transferrin
or lecithin (see Table 3).

| | | |
|---|---|---|
| + | 5 ml/liter | 200mM L glutamine |
| + | 50 mg/liter | L proline |
| + | 50 mg/liter | L threonine |
| + | 50 mg/liter | L methionine |
| + | 50 mg/liter | L cysteine |
| + | 50 mg/liter | L tyrosine |
| + | 25 mg/liter | L ascorbic acid |
| + | 0.062 mg.liter | Vitamin B6 |
| + | 1.36 mg.liter | Vitamin B12 |
| + | 2 mg/liter | Ferric citrate |
| + | 1 mg/liter | Zinc sulphate |
| + | 0.0025 mg.lit | Copper sulphate |
| + | 50,000 IU/liter | Polymyxin |
| + | 20,000 IU/liter | Neomycin |
| + | 3 µl/liter | Ethanolamine |
| + | 0.16 mg/liter | Putrescine |
| + | 5 mg/liter | Recombinant Insulin (Nucellin) |

Figure 4:
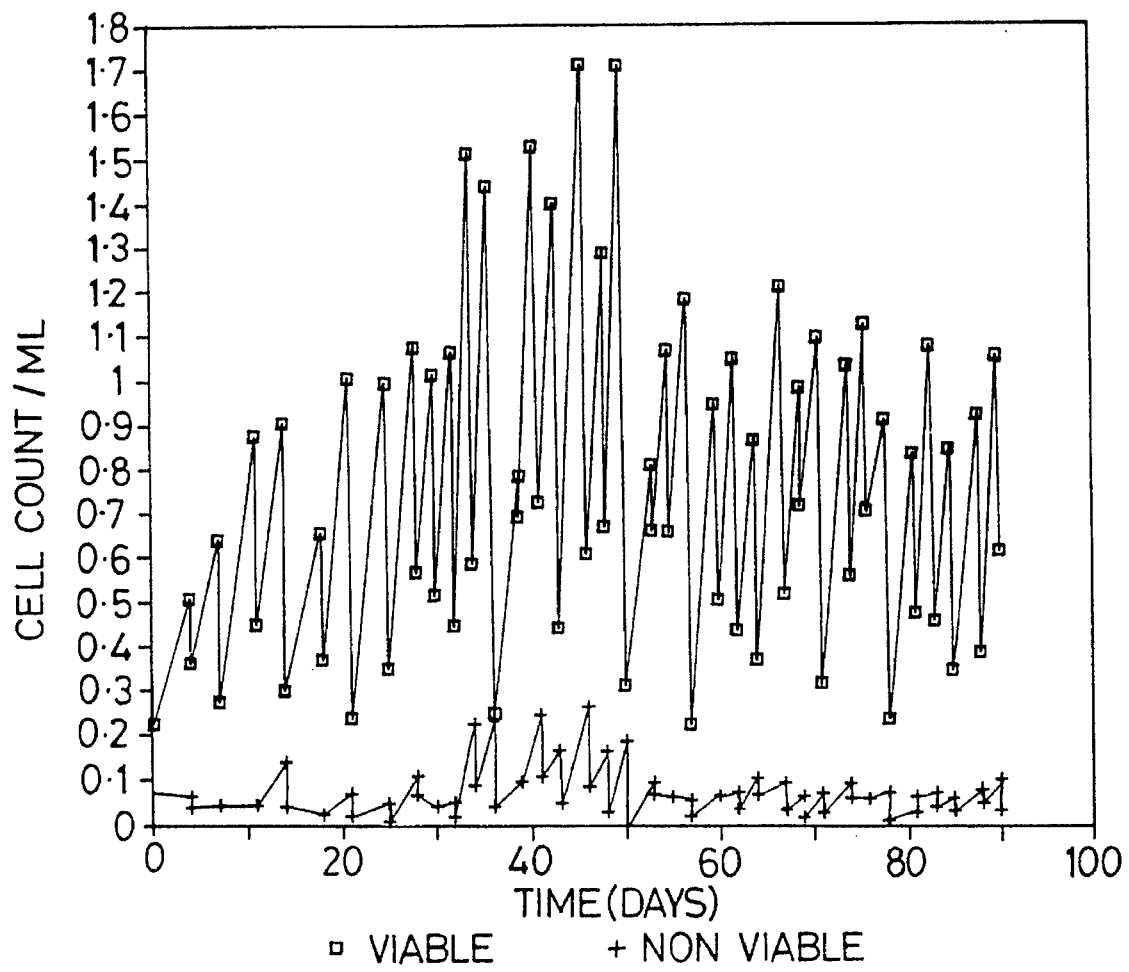
Figure 5:
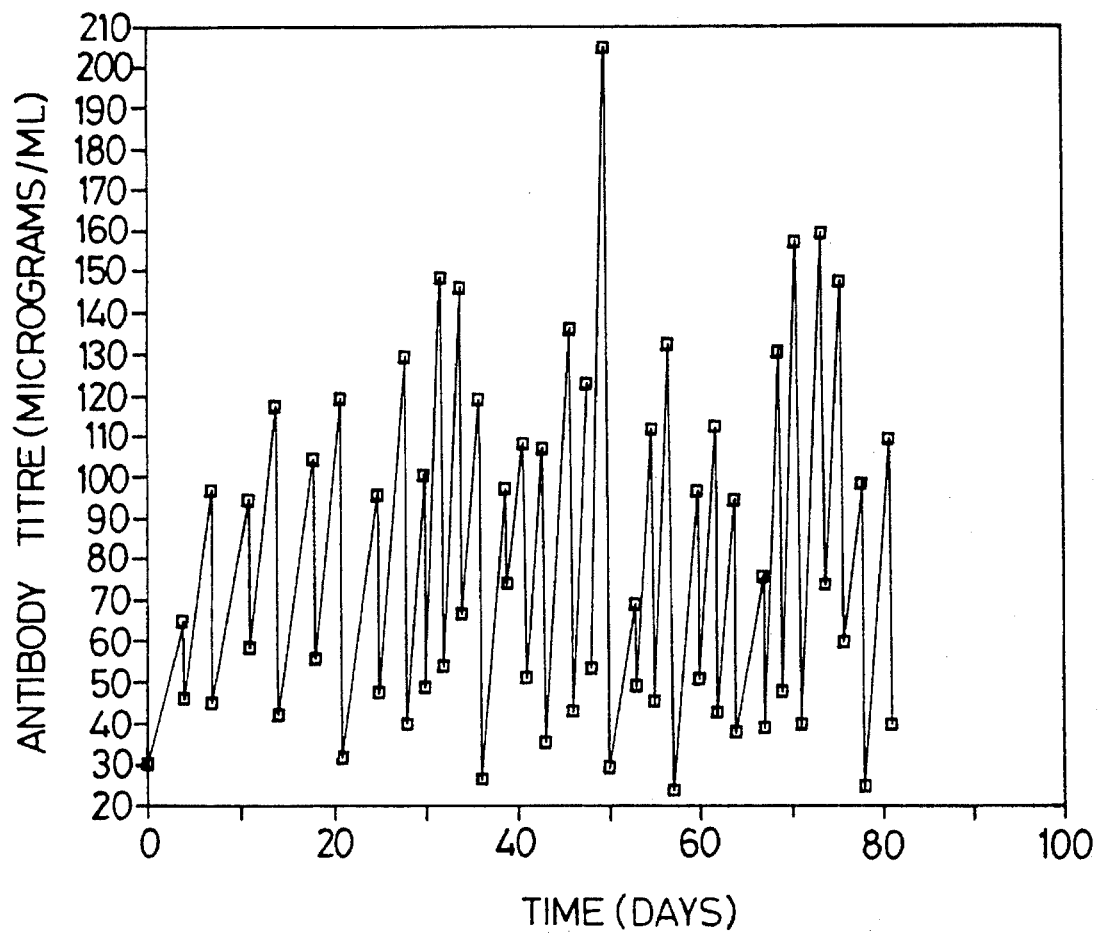

On day 53 the PEG was replaced with 0.1% pluronic F68. The resulting growth and antibody levels achieved are shown the the attached graphs (FIGS. 4 and 5), and demonstrate the capacity of the invention to allow protein-free production of antibody in excess of 100 µg/ml in fermenters.

EXAMPLE 5

Analysis of the Rate of Campath-1H Synthesis and Secretion from CHO Cells:

During the course of culturing the Campath-1H producing CHO cells of Example 3, it became clear that even when they reached confluence, antibody levels continued to accumulate, with time, in the culture medium. To determine whether this was possibly a consequence of intracellular accumulation coupled to slow secretion, the rates of Campath-1H synthesis and secretion were measured using A39 cells. These analyses were performed over 3–4 consecutive days on cells which were either in growth phase, or confluent stationary phase. For the cells in either growth state, the results were identical, and data is presented only for the immuno-precipitated radiolabelled Campath-1H produced from stationary cells.

Figure 2:
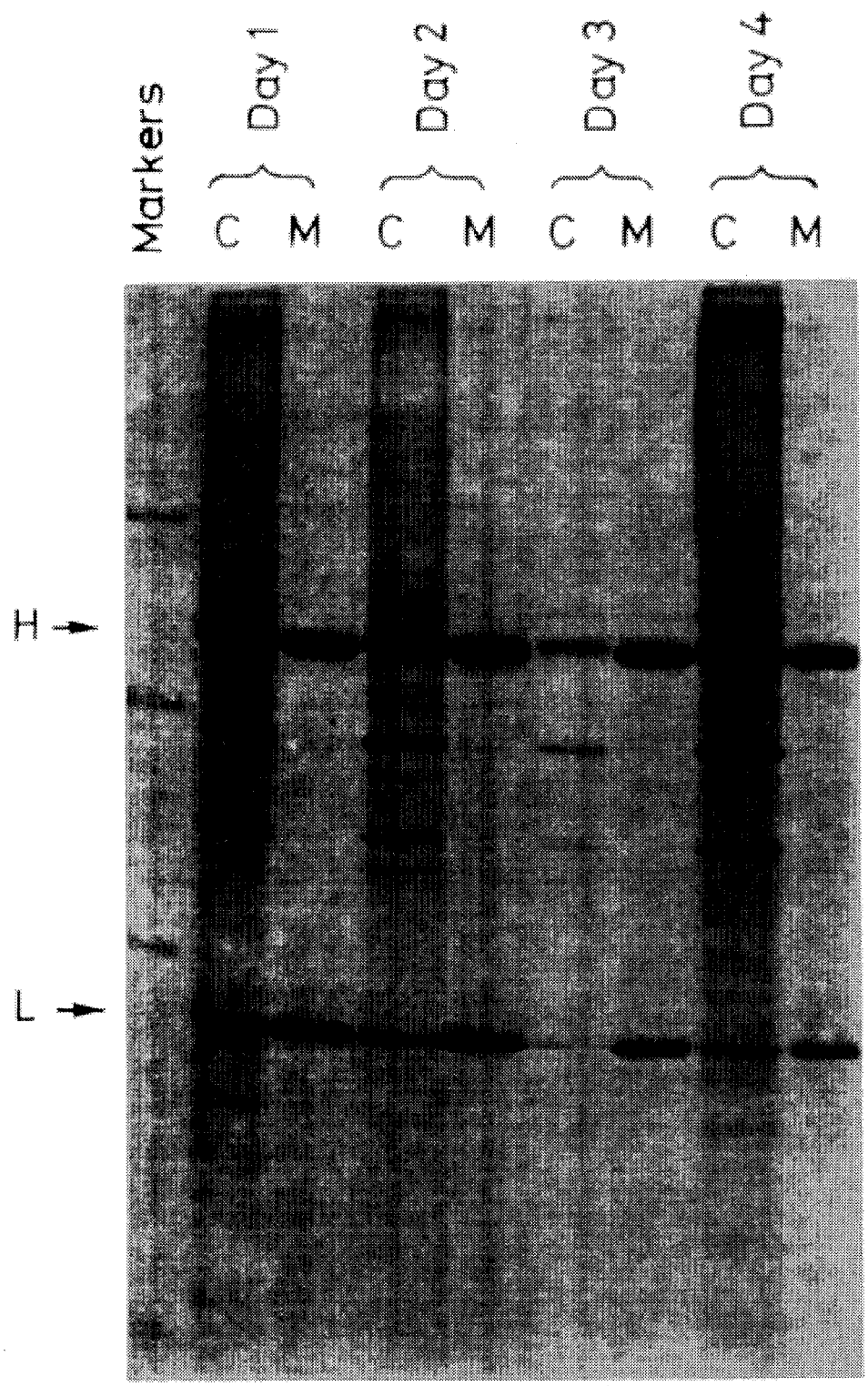
Figure 3:
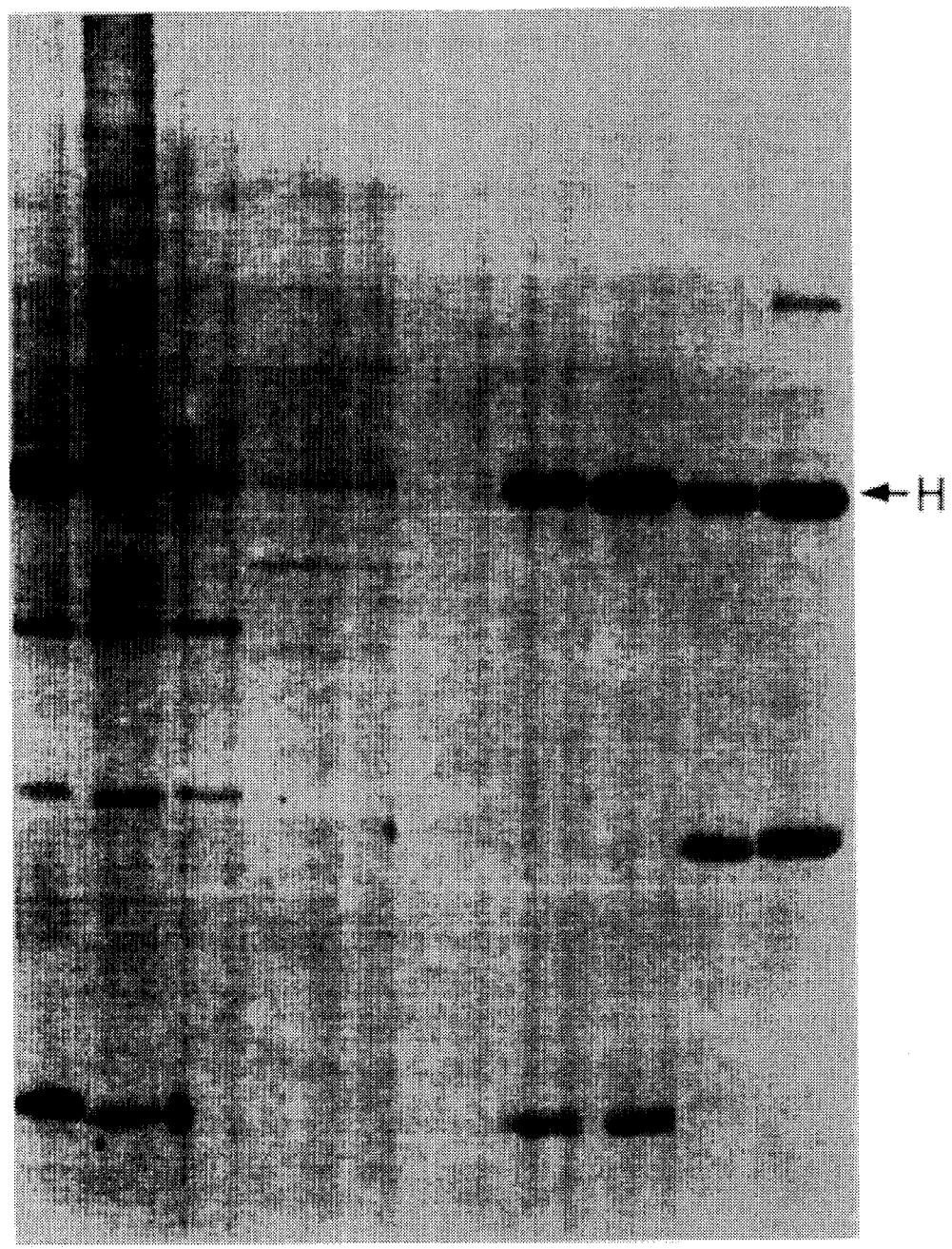

The rate of antibody synthesis was measured by pulsing the cells for a short period with [S$^{35}$]-methionine on each of four consecutive days, and then examining the quantity, and distribution, of immuno-precipitated material. In FIG. 2, it is clear that the rate of synthesis is equally high at all time points measured. Furthermore, even by the end of this short pulse, in each case, more than half of the newly synthesized Campath-1H is already present in the medium suggesting rapid secretion. This was confirmed by the data shown in FIG. 3, in which parallel cells were similarly pulsed, and the distribution of the radiolabelled Campath-1H chased over a three day period. Within 24 hours, virtually all of the cellular radiolabelled antibody has been chased into the medium, where it remained stable for the duration of the experiment. This demonstrates that even when the recombinant CHO cells remain stationary for long periods, the rates of Campath-1H synthesis and secretion are not diminished.

Campath-1H ELISA assay. Microtiter plates were coated with anti-human IgG and incubated with the assay sample (in culture medium). Antibody detection was visualized by using an anti-human gamma chain specific peroxidase conjugate.

Analysis of rates of Campath-1H synthesis and secretion. Cells from Example 3 were grown to confluence in 3 cm tissue culture wells, then incubated for 30 minutes in methionine-free Dulbeccos's MEM containing 10% fetal calf serum. Following this, the cells were labelled in the presence of 120 µCi/ml [$^{35}$S] methionine (>800 Ci/mmol; Amersham) for the appropriate time period, then either harvested and lysed in 500 µl of NP-40 lysis buffer, or incubated further in normal growth medium. Then 125 µl aliquots of cell lysate or culture medium were immuno-precipitated using goat anti-human IgG (heavy chain specific; Sigma) and 10% protein-A Sepharose (Pharmacia). Samples were then separated on 10% SDS-PAGE reducing gels according to Laemmli and the signals amplified with Enhance (NEN-Dupont). The dried gels were then autoradiographed overnight.

Biological assays for functional CHO-glycosylated Campath 1H

Complement lysis assay for Campath 1H

The complement lysis assay is a measure of antibody function expressed as specific activity, determined by the ability of a CHO-glycosylated antibody of known concentration to bind to a pre-determined number of cells and effect cell lysis. The assay is carried out on Campath 1H from Example 4 using Karpas 422 cells (established from B-cell non-Hodgkin lymphoma cell line—Dyer et al., (1990) Blood, 75 704–714) expressing Campath antigen on the cell surface. 12×10$^7$ cells were loaded with radiolabel by incubating for 2 hours at 37° C. in a CO$_2$ incubator in the presence of 600 µCi of 51 Cr (sodium chromate).

5.3 ml of the loaded cells in medium (total volume 23.5 ml), were added to 12.5 ml of normal human serum and 150 µl of the mixture were pipetted into the wells of a microtitre plate.

50 µl samples of the final eluate from three purification runs were mixed with the cells and incubated for 30 minutes at 4° C. followed by 90 minutes at 37° C. The culture was centrifuged at 2000 rpm for 5 minutes and the radioactivity in 100 µl of cell supernatant was counted on a gamma counter. Complement lysis activity in Kilo Units/ml was calculated from a standard curve of a reference preparation (1000 Units/ml).

The results are set out in Table 5.

The concentration of Campath 1H in the 50 µl samples of final eluate was estimated using samples in PBS pH 7.2 read on a spectrophotometer at 280 nm. The results are expressed in Table 3 as optical density in mg/ml.

From this data the specific activity:

$$\frac{KU/ml}{OD}$$

is determined.

TABLE 5

| Sample | Complement lysis Kilo Units/ml | Protein Conc mg/ml | Specific Activity |
|---|---|---|---|
| A | 11.2 | 11.1 | 1.0 |
| B | 14.8 | 14.2 | 1.0 |
| C | 13.7 | 13.6 | 1.0 |

The results indicate that CHO-glycosylated Campath 1H is functional.

Treatment of an individual with CHO-glycosylated Campath 1H

An individual diagnosed as having severe T-cell mediated inflammation of the joints (immobilising polyarthritis, pleuritis, abdominal pains) over five years requiring long periods of hospitalisation was treated with CHO derived Campath 1H from Example 4 using the following regime:

2 mg per day over 6 days by intravenous injection 10 mg per day over subsequent 6 days by intravenous injection.

During the second 6 day treatment there was a significant symptomatic improvement. By the end of the second period the joint inflammation was much improved and a skin abscess had cleared with antibiotic treatment. Thirty days after the end of the treatment the individual was discharged.

Approximately 9 months after the initial treatment, the individual suffered a relapse with multiple joint involvement. After initial testing for sensitivity with a low dose, the individual was given a further course of treatment with 10 mg/day Campath 1H for 10 days with significant improvement.

EXAMPLE 6

EXPRESSION OF HUMANISED ANTI-CD4 ANTIBODY FROM CHO CELLS

Construction of the expression vector pBanl; modification of p342–12

The complementarily determining regions from a rat IgG2b raised against human CD4 (The New England Journal of Medicine 1990 323: 250–254) were grafted onto human heavy and light chain frameworks (Winter et al, *Nature*, 1988, 322 323–327).

The cDNA encoding the humanised CD4 light chain was cloned into pLD9 [Page and Sydenham, M. A. 199 Biotechnology 9 64–68]. The resulting plasmid was designated p2110. The humanised CD4 heavy chain was sequenced and cloned into a modified version of plasmid p342–12 (Law M-F., Byrne, J. C. and Hinley, P. M. 1983 *Mol. Cell. Biol.* 3 2110–2115). Plasmid p342–12 was digested with BamH1 to remove the 7.4 kbp fragment containing part of the BPV-1 genome. The backbone containing the β-lactamase gene and the neomycin resistance gene under the control of the mouse metallothionine promoter was purified and religated at the BamH1 site. This plasmid was digested with HinDIII, incubated with the large fragment of DNA polymerase I to remove the HinDIII site and then religated. The β-actin expression cassette, containing the β-actin promoter immediately upstream of a unique HinDIII site followed by the polyadenylation signal, was cloned into the BamHI site of the modified p342–12 plasmid to generate pBan1.

Plasmid pBan1, therefore, consisted of the neomycin resistance gene, the β-lactamase gene and the β-actin expression cassette containing the unique HinDIII site. The cDNA encoding the humanised heavy chain was cloned into this site and the resulting plasmid containing the correctly orientated insert was designated pBanCD4H. Thus, p2110 and pBanCD4H contained a different selectable marker and co-transfection into recipient dhfr– CHO cells would permit the direct selection and isolation of dhfr$^+$/neo$^r$ colonies. Cells exhibiting this phenotype should express functional antiCD4 antibody and could be amplified to elevate the antibody titres.

Expression of anti-CD4 antibody in CHO cells a) Cell culture methods.

The dhfr– CHO line DUK-B11 [Urlaub, G. and Chasin, L. A. 1980 Proc.Natl.Acad.Sci.USA 77 4216–4220] was propagated in Iscoves MEM medium supplemented with 10% foetel bovine serum and 4 μg each of hypoxanthine and thymidine (all Flow). After transfection, transformants were selected in the medium described above except that the hypoxanthine/thymidine were omitted and dialysed foetal bovine serum was used. In addition, G418 was included at 500 μg/ml. To induce spontaneous amplification of sequences containing and flanking the dhfr gene, MTX was added to a concentration of 0.1 μM.

b) Transfection and amplification

The dhfr– CHO cell line DUK-B11 was co-transfected with 5 μg of p2110 and 5 μg of pBanCD4H using the transfectam reagent under the conditions recommended by the manufacturer. Transformants were selected for the dhfr$^+$/neo$^r$ phenotype as described above. Several hundreds of transformants were observed and pooled. Initital titres indicated that the first round basal transformants were secreting about 0.1 μg/ml/day. This pooled population was then cultured in the presence of 0.1 μM MTX for about 14 days. Resistant colonies were again pooled and assayed. Expression had increased some 100 fold, the pooled, amplified colonies producing about 10–12 μg/ml/day. In order to obtain stable, clonal cell lines giving high antibody titres, the resistant pools were cloned by limiting dilution in 96-well plates. Fifty single colonies were identified and assayed and the four lines giving the highest titres propagated. This process of identifying highly expressing clones within the resistant population produced a line designated D419 which expressed the anti-CD4 antibody at about 20 μg/ml/day.

Characterisation of dhfr$^+$/neo$^r$ cell lines i) Determination of copy number and steady state transcription levels by slot blot analysis of DNA and RNA.

Whole cell RNA and DNA was prepared from the various stages of amplification as described by Maniatis et al. [1982 Molecular Cloning. A Laboratory Manual. Cold Spring Harbour Laboratory, Cold Spring Harbour, N.Y.]. After fixing onto nitrocellulose filters, the nucleic acids were probed with [$^{32}$-P]-αATP labelled DNA sequences of the heavy chain, the dhfr gene and the β-actin gene as a control "housekeeping" gene to eliminate artifacts due to loading errors.

Inititally, the uncloned 0.1 μM MTX amplified pool was compared to the first round unamplified transformants and the untransformed parental B11 cells, with the probes described. Accordingly, no DNA signal was detected in the parental line when probed with the heavy chain but a weak signal was detected for dhfr. This is due to the single, non-functional dhfr allele in the B11 cell line. As a result, no RNA signal was detected with either probe. In contrast, a strong signal was detected with both probes on RNA and DNA in the primary transformants which reflects the start of expression. A very significant increase in copy number and steady state levels of RNA of heavy chain and dhfr is observed in the uncloned amplified pool. This accurately correlates with the observed increase in expression. Steady state levels of β-actin RNA were consistent in all three lines examined.

A similar comparison was made between the four highest expressing cloned cell lines. A strong signal was detected on both the RNA and the DNA blots. However, although the DA19 line was expressing twice as much antibody as a line designated D423, this difference was not in either the copy number or steady state levels of RNA. There are two possible explanations for this observation; the first is that the DNA in the DA19 line has integrated at a site in the genome at which it is under the influence of an enhancer. However, this presumably would be reflected in elevated levels of RNA. The more likely explanation is that in the replication and duplication of the tandem arrays in the line D423, some of the copies of the dhfr/antibody cassette have undergone re-arrangement and are non-functional and truncated. This is not uncommon since the site of integration of heterologous genes is often at breakpoints in the chromosomes such as telomeres which are known to be "hot spots" for such re-arrangements. This could be resolved by Northern and Southern analysis.

ii) Protein synthesis and secretion of anti-CD4 antibody in the D419 line

The clonal D419 line was labelled with $^{35}$S-methionine and cysteine and the intracellular and secreted antibody extracted by immunoprecipitation with appropriate antibodies. Following electrophoresis on reducing SDS-PAGE gels, the gels were dried and the signal detected by autoradiography.

It was clear from the result that both heavy and light chain are efficiently synthesised. Intracellularly, there need not be sto chiometry between heavy and light chains since the two associate as they pass through the secretory organelles. However, close stochiometry is observed in the secreted material.

I claim:

1. In a method for treating a human suffering from cancer by administering a therapeutically effective amount of a whole glycosylated recombinant human, chimeric, CDR grafted or bispecific antibody effective in treating said cancer, wherein the improvement comprises an antibody glycosylated by a Chinese hamster ovary cell.

2. A method in accordance with claim 1, wherein the cancer is non-Hodgkins lymphoma.

3. A method in accordance with claim 1, wherein the cancer is multiple myeloma.

4. A method in accordance with claim 3, wherein the antibody specifically recognizes a T cell marker.

5. A method in accordance with claim 4, wherein the antibody is an anti-CDw52 antibody.

6. A method in accordance with claim 1, wherein the antibody specifically recognizes a cancer cell marker antigen.

7. A method in accordance with claim 6, wherein the antibody is an anti-CD33 antibody or an anti-CD38 antibody.

8. A method in accordance with claim 1, wherein the antibody is administered in a daily dose of about 1 mg to about 10 mg.

9. A method in accordance with claim 1, wherein the antibody is administered for a period of about 1 to about 30 days.

* * * * *

UNITED STATES PATENT AND TRADEMARK OFFICE
Certificate

Patent No. 5,545,405                                                    Patented: August 13, 1996

On petition requesting issuance of a certificate for correction of inventorship pursuant to 35 U.S.C. § 256, it has been found that the above-identified patent, through error and without any deceptive intent, improperly sets forth the inventorship.

Accordingly, it is hereby certified that the correct inventorship of this patent is: Martin John Page and James Scott Crowe.

Signed and Sealed this Seventeenth Day of June, 1997.

CHRISTINA CHAN
*Supervisory Patent Examiner*
Art Unit 1816